United States Patent
Gale et al.

(10) Patent No.: US 8,658,081 B2
(45) Date of Patent: Feb. 25, 2014

(54) METHODS OF FABRICATING STENTS WITH ENHANCED FRACTURE TOUGHNESS

(75) Inventors: David C. Gale, Kennesaw, GA (US);
Bin Huang, Pleasanton, CA (US);
Timothy Limon, Cupertino, CA (US);
Vincent J. Gueriguian, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 423 days.

(21) Appl. No.: 12/845,536

(22) Filed: Jul. 28, 2010

(65) Prior Publication Data
US 2010/0289191 A1 Nov. 18, 2010

Related U.S. Application Data

(60) Continuation of application No. 12/772,698, filed on May 3, 2010, which is a division of application No. 11/454,968, filed on Jun. 15, 2006, now Pat. No. 7,731,890.

(51) Int. Cl.
*B29C 49/08* (2006.01)

(52) U.S. Cl.
USPC .......... 264/534; 264/138; 264/400; 264/523; 623/1.15; 623/1.16

(58) Field of Classification Search
USPC ......... 264/138, 400, 523, 534; 623/1.15, 1.16
See application file for complete search history.

(56) References Cited

U.S. PATENT DOCUMENTS

| | | | |
|---|---|---|---|
| 640,774 A | * | 1/1900 | Kemper .......................... 49/160 |
| 3,636,956 A | | 1/1972 | Schneider |
| 4,547,416 A | | 10/1985 | Reed et al. |
| 4,698,196 A | | 10/1987 | Fabian |
| 4,702,884 A | | 10/1987 | Goldstein |
| 4,957,687 A | | 9/1990 | Akman et al. |
| 4,987,025 A | | 1/1991 | Shiraki et al. |
| 5,087,394 A | | 2/1992 | Keith |
| 5,108,416 A | | 4/1992 | Ryan et al. |
| 5,116,365 A | | 5/1992 | Hillstead |
| 5,147,302 A | | 9/1992 | Euteneuer et al. |
| 5,342,348 A | * | 8/1994 | Kaplan ..................... 604/891.1 |
| 5,500,013 A | | 3/1996 | Buscemi et al. |
| 5,628,786 A | | 5/1997 | Banas et al. |
| 5,670,161 A | | 9/1997 | Healy et al. |
| 5,868,782 A | * | 2/1999 | Frantzen ..................... 623/1.15 |

(Continued)

FOREIGN PATENT DOCUMENTS

| | | |
|---|---|---|
| EP | 0 583 170 | 2/1994 |
| EP | 1 800 628 | 6/2007 |

(Continued)

OTHER PUBLICATIONS

Declaration under 37 C.F.R. § 1.132 by Bin Huang and David Gale filed in U.S. Appl. No. 11/417,376, executed Jul. 22, 2010, 5 pgs.

(Continued)

*Primary Examiner* — Christina Johnson
*Assistant Examiner* — Saeed Huda
(74) *Attorney, Agent, or Firm* — Squire Sanders (US) LLP

(57) ABSTRACT

Stents and methods of manufacturing a stents with enhanced fracture toughness are disclosed.

15 Claims, 7 Drawing Sheets

(56) References Cited

U.S. PATENT DOCUMENTS

| | | | |
|---|---|---|---|
| 5,891,386 A | 4/1999 | Deitermann et al. | |
| 6,500,146 B1 | 12/2002 | Pinchuk et al. | |
| 6,530,950 B1* | 3/2003 | Alvarado et al. | 623/1.13 |
| 6,572,813 B1 | 6/2003 | Zhang et al. | |
| 6,626,939 B1 | 9/2003 | Burnside et al. | |
| 6,634,426 B2* | 10/2003 | McCoy et al. | 166/254.1 |
| 6,638,300 B1* | 10/2003 | Frantzen | 623/1.15 |
| 6,645,422 B2 | 11/2003 | Jung et al. | |
| 7,066,952 B2 | 6/2006 | Igaki | |
| 7,070,615 B1 | 7/2006 | Igaki | |
| 7,083,639 B2 | 8/2006 | Guinan et al. | |
| 7,115,691 B2* | 10/2006 | Alvarado et al. | 526/245 |
| 7,128,868 B2 | 10/2006 | Eidenschink | |
| 7,374,570 B2* | 5/2008 | Alvarado et al. | 623/1.14 |
| 7,666,342 B2 | 2/2010 | Limon et al. | |
| 7,731,890 B2* | 6/2010 | Gale et al. | 264/534 |
| 2001/0014821 A1 | 8/2001 | Juman et al. | |
| 2002/0035394 A1* | 3/2002 | Fierens et al. | 623/1.13 |
| 2002/0041059 A1 | 4/2002 | Jung et al. | |
| 2002/0077592 A1 | 6/2002 | Barry | |
| 2002/0138133 A1 | 9/2002 | Lenz et al. | |
| 2002/0151965 A1* | 10/2002 | Roth | 623/1.17 |
| 2003/0028241 A1 | 2/2003 | Stinson | |
| 2003/0028246 A1 | 2/2003 | Palmaz et al. | |
| 2003/0050687 A1 | 3/2003 | Schwade et al. | |
| 2003/0055488 A1 | 3/2003 | Igaki | |
| 2003/0083732 A1 | 5/2003 | Stinson | |
| 2003/0149470 A1* | 8/2003 | Alvarado et al. | 623/1.13 |
| 2003/0187158 A1 | 10/2003 | Preuschen et al. | |
| 2003/0208254 A1 | 11/2003 | Shortt | |
| 2003/0226833 A1 | 12/2003 | Shapovalov et al. | |
| 2004/0000361 A1* | 1/2004 | Trozera | 148/593 |
| 2004/0098090 A1 | 5/2004 | Williams et al. | |
| 2004/0181271 A1 | 9/2004 | DeSimone et al. | |
| 2004/0215326 A1* | 10/2004 | Goodson et al. | 623/1.16 |
| 2005/0004656 A1* | 1/2005 | Das | 623/1.16 |
| 2005/0004659 A1* | 1/2005 | Von Oepen et al. | 623/1.16 |
| 2005/0004662 A1* | 1/2005 | Von Oepen et al. | 623/1.42 |
| 2005/0004663 A1 | 1/2005 | Llanos et al. | |
| 2005/0102022 A1* | 5/2005 | Solovay et al. | 623/1.13 |
| 2005/0137678 A1 | 6/2005 | Varma | |
| 2005/0177130 A1 | 8/2005 | Konstantino et al. | |
| 2005/0187615 A1 | 8/2005 | Williams et al. | |
| 2005/0196485 A1 | 9/2005 | Cass et al. | |
| 2005/0203617 A1* | 9/2005 | Forster et al. | 623/2.14 |
| 2006/0020330 A1* | 1/2006 | Huang et al. | 623/1.49 |
| 2006/0076708 A1 | 4/2006 | Huang et al. | |
| 2006/0095115 A1* | 5/2006 | Bladillah et al. | 623/1.16 |
| 2006/0136040 A1* | 6/2006 | Burgermeister et al. | 623/1.16 |
| 2006/0211952 A1 | 9/2006 | Kennedy | |
| 2006/0224226 A1 | 10/2006 | Huang et al. | |
| 2006/0235506 A1* | 10/2006 | Ta et al. | 623/1.16 |
| 2006/0259122 A1* | 11/2006 | Eliseev | 623/1.12 |
| 2007/0038290 A1* | 2/2007 | Huang et al. | 623/1.16 |
| 2007/0073016 A1* | 3/2007 | Alvarado et al. | 526/245 |
| 2007/0073376 A1* | 3/2007 | Krolik et al. | 623/1.11 |
| 2007/0135892 A1* | 6/2007 | Burgermeister et al. | 623/1.16 |
| 2007/0135896 A1* | 6/2007 | Burgermeister et al. | 623/1.16 |
| 2007/0135898 A1* | 6/2007 | Burgermeister et al. | 623/1.16 |
| 2007/0135899 A1* | 6/2007 | Burgermeister et al. | 623/1.16 |
| 2007/0135983 A1* | 6/2007 | McDonald et al. | 701/45 |
| 2007/0135985 A1* | 6/2007 | Berry et al. | 701/50 |
| 2007/0156226 A1* | 7/2007 | Chew et al. | 623/1.12 |
| 2007/0200229 A1* | 8/2007 | Daubenspeck et al. | 257/723 |
| 2007/0213810 A1* | 9/2007 | Newhauser et al. | 623/1.16 |
| 2007/0216619 A1* | 9/2007 | Hung | 345/87 |
| 2007/0253996 A1 | 11/2007 | Bin et al. | |
| 2007/0253999 A1 | 11/2007 | Huang et al. | |
| 2007/0265698 A1* | 11/2007 | Pienknagura | 623/1.16 |
| 2007/0282431 A1 | 12/2007 | Gale et al. | |
| 2007/0282433 A1 | 12/2007 | Limon et al. | |
| 2007/0283552 A1* | 12/2007 | Gale et al. | 29/515 |
| 2007/0290412 A1 | 12/2007 | Capek et al. | |
| 2007/0293938 A1* | 12/2007 | Gale et al. | 623/1.15 |
| 2008/0001333 A1 | 1/2008 | Kleine et al. | |
| 2008/0300670 A1 | 12/2008 | Gueriguian et al. | |
| 2009/0001633 A1 | 1/2009 | Limon et al. | |
| 2009/0005854 A1 | 1/2009 | Huang et al. | |
| 2009/0012598 A1 | 1/2009 | Abbate et al. | |
| 2009/0146348 A1* | 6/2009 | Huang et al. | 264/573 |
| 2009/0264979 A1* | 10/2009 | Kao et al. | 623/1.11 |
| 2010/0256740 A1* | 10/2010 | Limon et al. | 623/1.16 |
| 2011/0224778 A1* | 9/2011 | Gale et al. | 623/1.16 |

FOREIGN PATENT DOCUMENTS

| | | |
|---|---|---|
| GB | 2 102 827 | 2/1983 |
| WO | WO 97/32546 | 9/1997 |
| WO | WO 00/12147 | 3/2000 |
| WO | WO 01/15633 | 3/2001 |
| WO | WO 03/034940 | 5/2003 |
| WO | WO 2004/067262 | 8/2004 |
| WO | WO 2006/014747 | 2/2006 |

OTHER PUBLICATIONS

Answers.com blow molding; retrieved from www.answers.com/blow%20molding#Stretch_blow_molding, Jun. 26, 2009, 11 pgs.
www.engineeringtoolbox.com/thermal/conductivity/d_429.html, Jun. 26, 2009, 4 pgs.
International Search Report for PCT/US2007/013915 filed Jun. 13, 2007, mailed Jan. 7, 2008, 4 pgs.
Middleton et al., Synthetic Biodegradable Polymers as Medical Devices, Medical Device and Diagnostic Industry; downloaded from: www.mddionline.com/article/synthetic-biodegradable-polymers-medical-devices, Mar. 1998, 4pgs.
U.S. Appl. No. 10/881,554, filed Jun. 29, 2004, Abbate et al.
U.S. Appl. No. 10/956,759, filed Sep. 30, 2004, Durcan.
U.S. Appl. No. 10/956,910, filed Sep. 30, 2004, Huang et al.
U.S. Appl. No. 10/956,911, filed Sep. 30, 2004, Durcan.

* cited by examiner

METHODS OF FABRICATING STENTS WITH ENHANCED FRACTURE TOUGHNESS

CROSS-REFERENCE

This is a continuation of application Ser. No. 12/772,698 filed on May 3, 2010 which is a divisional application of 11/454,968 filed on Jun. 15, 2006.

BACKGROUND OF THE INVENTION

1. Field of the Invention

This invention relates to methods of fabricating stents having selected mechanical properties.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

However, there are potential shortcomings in the use of polymers as a material for implantable medical devices, such as stents. There is a need for a manufacturing process for a stent that addresses such shortcomings so that a polymeric stent can meet the clinical and mechanical requirements of a stent.

SUMMARY OF THE INVENTION

Certain embodiments of the present invention include a stent comprising a cylindrically aligned bending element formed by a first bar arm and a second bar arm, the angle between the bar arms being greater than about 90°, wherein the stent is fabricated from a tube radially expanded by at least about 400%.

Further embodiments of the present invention include a stent comprising a cylindrically aligned bending element formed by a first bar arm and a second bar arm, an angle between each of the bar arms and the circumferential direction being less than about 45°, wherein the stent is fabricated from a tube radially expanded by at least 500%.

Additional embodiments of the present invention include a stent comprising a plurality of cylindrically aligned bending elements, the angles between the bending elements being greater than about 90°.

Other embodiments of the present invention include a method of fabricating a stent comprising: radially expanding a tube to at least about 400%; and cutting a pattern comprising a cylindrically aligned bending element formed by a first bar arm and a second bar arm, the angle between the bar arms being greater than about 90°, wherein the stent is fabricated from a tube radially expanded by at least about 400%.

Some embodiments of the present invention include a method for fabricating a stent comprising: conveying a gas into a poly(L-lactide) tube disposed within a cylindrical mold to increase a pressure inside the tube, wherein the increased pressure radially expands the polymeric tube to conform to the inside surface of the mold; applying tension along the axis of the tube to axially extend the tube; and fabricating a stent from the radially expanded and axially extended tube.

Certain embodiment of the present invention include a method for fabricating a stent comprising: processing a polymer form to increase the Tg of the polymer at least about 10° C.; and fabricating a stent from the processing form.

Additional embodiments of the present invention include a method for fabricating a stent comprising: processing a polymer form so as to increase the Tg of the polymer to at least about 40° C. above ambient temperature to allow storage of the processed polymer at the ambient temperature; and fabricating a stent from the processed polymer.

Other embodiments of the present invention include a method for fabricating a stent comprising: processing a polymer form so as to increase the Tg of the polymer to at least about 20° C. above a crimping temperature.

DETAILED DESCRIPTION OF THE INVENTION

The various embodiments of the present invention relate to polymeric stents and methods of fabricating polymeric stents with favorable mechanical properties. The present invention can be applied to devices including, but is not limited to, self-expandable stents, balloon-expandable stents, stent-grafts, and grafts (e.g., aortic grafts).

Figure 1:
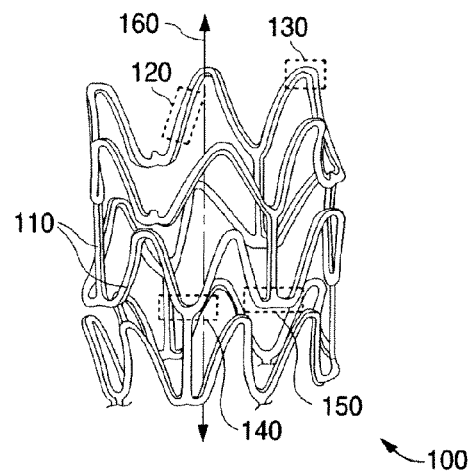
FIG. 1 depicts a stent.

A stent can have a scaffolding or a substrate that includes a pattern of a plurality of interconnecting structural elements or struts. FIG. 1 depicts an example of a view of a stent 100. Stent 100 has a cylindrical shape with an axis 160 and includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1. The variation in stent patterns is virtually unlimited.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

The pattern of stent 100 in FIG. 1 varies throughout its structure to allow radial expansion and compression and longitudinal flexure. A pattern may include portions of struts that are straight or relatively straight, an example being a portion 120. In addition, patterns may include bending elements 130, 140, and 150.

Bending elements bend inward when a stent is crimped to allow radial compression. Bending elements also bend outward when a stent is expanded to allow for radial expansion. After deployment, a stent is under static and cyclic compressive loads from the vessel walls. Thus, bending elements are subjected to deformation during use. "Use" includes, but is not limited to, manufacturing, assembling (e.g., crimping stent on a catheter), delivery of stent into and through a bodily lumen to a treatment site, and deployment of stent at a treatment site, and treatment after deployment.

As indicated above, a stent has certain mechanical requirements. A stent must have sufficient radial strength to withstand structural loads, namely radial compressive forces, imposed on the stent as it supports the walls of a vessel. In addition, the stent must possess sufficient flexibility to allow for crimping, expansion, and cyclic loading. Also, a sufficiently low profile, that includes diameter and size of struts, is important. As the profile of a stent decreases, the easier is its delivery, and the smaller the disruption of blood flow.

Polymers tend to have a number of shortcomings for use as materials for stents. One such shortcoming is that many biodegradable polymers have a relatively low modulus, and thus relatively low radial strength. Compared to metals, the strength to weight ratio of polymers is smaller than that of metals. A polymeric stent with inadequete radial strength can result in mechanical failure or recoil inward after implantation into a vessel. To compensate for the relatively low modulus, a polymeric stent requires significantly thicker struts than a metallic stent, which results in an undesirably large profile.

Another shortcoming of polymers is that many polymers, such as biodegradable polymers, tend to be brittle under physiological conditions or conditions within a human body. Specifically, such polymers can have a Tg, which is defined below, above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Other potential problems with polymeric stents include creep, stress relaxation, and physical aging. Creep refers to the gradual deformation that occurs in a polymeric construct subjected to an applied load. It is believed that the delayed response of polymer chains to stress during deformation causes creep behavior. Creep occurs even when the applied load is constant. Creep can cause an expanded stent to retract radially inward, reducing the effectiveness of a stent in maintaining desired vascular patency. The rate at which polymers creep depends not only on the load, but also on temperature. In general, a loaded construct creeps faster at higher temperatures.

Stress relaxation is also a consequence of delayed molecular motions as in creep. Contrary to creep, however, which is experienced when the load is constant, stress relaxation occurs when deformation (or strain) is constant and is manifested by a reduction in the force (stress) required to maintain a constant deformation Physical aging, as used herein, refers to densification in the amorphous regions of a semi-crystalline polymer. Physical aging of semi-crystalline polymers that have glass transition temperatures (Tg) above their normal storage temperature, which, for the purposes of this invention is room temperature, i.e., from about 15° C. to about 35° C., occurs primarily through the phenomenon known as densification. Densification occurs when polymer chains rearrange in order to move from a non-equilibrium state to an equilibrium state. The reordering of polymer chains tends to increase the modulus of the polymer resulting in a brittle or more brittle polymer.

Thus, physical aging results in an increase in brittleness of a polymer which can result in cracking of struts upon crimping and deployment. Since physical aging results from densification of amorphous regions of a polymer, an increase in crystallinity can reduce or inhibit physical aging.

However, it is well known by those skilled in the art that the mechanical properties of a polymer can be modified through various processing techniques, such as, by applying stress to a polymer. James L. White and Joseph E. Spruiell, Polymer and Engineering Science, 1981, Vol. 21, No. 13. The application of stress can induce molecular orientation along the direction of stress which can modify mechanical properties along the direction of applied stress. For example, strength and modulus are some of the important properties that depend upon orientation of polymer chains in a polymer. Molecular orientation refers to the relative orientation of polymer chains along a longitudinal or covalent axis of the polymer chains.

A polymer may be completely amorphous, partially crystalline, or almost completely crystalline. A partially crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions. An oriented amorphous region also tends to have high strength and high modulus along an axis of alignment of polymer chains. Additionally, for some polymers under some conditions, induced alignment in an amorphous polymer may be accompanied by crystallization of the amorphous polymer into an ordered structure. This is known as stress induced crystallization.

As indicated above, due to the magnitude and directions of stresses imposed on a stent during use, it is important for the mechanical stability of the stent to have suitable mechanical properties, such as strength and modulus, in the axial and circumferential directions. Therefore, it can be advantageous to modify the mechanical properties of a tube, to be used in the fabrication of a stent, by induced orientation from applied stress in the axial direction, circumferential direction, or both. Since highly oriented regions in polymers tend to be associated with higher strength and modulus, it may be desirable to incorporate processes that induce alignment of polymer chains along one or more preferred axes or directions into fabrication of stents.

Therefore, it can be desirable to fabricate a stent from a polymeric tube with induced orientation in the axial direction and in the circumferential direction. A biaxial oriented tube may be configured to have desired strength and modulus in both the circumferential and axial directions.

The degree of radial expansion, and thus induced radial orientation and strength, of a tube can be quantified by a radial expansion (RE) ratio:

$$\frac{\text{Outside Diameter (OD) of Expanded Tube}}{\text{Original Inside Diameter (ID) of Tube}}$$

The RE ratio can also be expressed as a percent expansion:

% Radial expansion=(RE ratio−1)×100%

Similarly, the degree of axial extension, and thus induced axial orientation and strength, may be quantified by an axial extension (AE) ratio:

$$\frac{\text{Length of Extended Tube}}{\text{Original Length of Tube}}$$

The AE ratio can also be expressed as a percent expansion:

% Axial expansion=(AE ratio−1)×100%

In some embodiments, a polymeric tube may be deformed by blow molding. In blow molding, a tube can be deformed or expanded radially by increasing a pressure in the tube by conveying a fluid into the tube. The polymer tube may be deformed or extended axially by applying a tensile force by a tension source at one end while holding the other end stationary. Alternatively, a tensile force may be applied at both ends of the tube. The tube may be axially extended before, during, and/or after radial expansion.

In some embodiments, blow molding may include first positioning a tube in a cylindrical member or mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube. Alternatively, the fluid temperature and pressure may be used to control the degree of radial deformation by limiting deformation of the inside diameter of the tube as an alternative to or in combination with using the mold.

The temperature of the tube can be heated to temperatures above the Tg of the polymer during deformation to facilitate deformation. The polymer tube may also be heated prior to, during, and subsequent to the deformation. In one embodiment, the tube may be heated by conveying a gas above ambient temperature on and/or into the tube. The gas may be the same gas used to increase the pressure in the tube. In another embodiment, the tube may be heated by translating a heating element or nozzle adjacent to the tube. In other embodiments, the tube may be heated by the mold. The mold may be heated, for example, by heating elements on, in, and/or adjacent to the mold.

Certain embodiments may include first sealing, blocking, or closing a polymer tube at a distal end. The end may be open in subsequent manufacturing steps. The fluid, (conventionally a gas such as air, nitrogen, oxygen, argon, etc.) may then be conveyed into a proximal end of the polymer tube to increase the pressure in the tube. The pressure of the fluid in the tube may act to radially expand the tube.

Additionally, the pressure inside the tube, the tension along the cylindrical axis of the tube, and the temperature of the tube may be maintained above ambient levels for a period of time to allow the polymer tube to be heat set. Heat setting may include maintaining a tube at a temperature greater than or equal to the Tg of the polymer and less than the Tm of the polymer for a selected period to time. The selected period of time may be between about one minute and about two hours, or more narrowly, between about two minutes and about ten minutes.

In heat setting, the polymer tube may then be cooled to below its Tg either before or after decreasing the pressure and/or decreasing tension. Cooling the tube helps insure that the tube maintains the proper shape, size, and length following its formation. Upon cooling, the deformed tube retains the length and shape imposed by an inner surface of the mold.

Properties of a polymer such as fracture toughness are affected by the overall degree of crystallinity and the number and size of crystal domains in a semi-crystalline polymer. It has been observed that fracture toughness is increased by having a large number of small crystal domains in a polymer surrounded by an amorphous domain. Such a crystal structure can also reduce or prevent creep, stress relaxation, and physical aging. In some embodiments, the size of crystal domains may be less than 10 microns, 4 microns, or, more narrowly, less than 2 microns. The overall crystallinity may be less than 50%, 40% or, more narrowly, less than 20%.

In certain embodiments, the temperature of the deformation process and/or heat setting can be used to control the crystallinity to obtain the desired crystal structure described above. In general, crystallization tends to occur in a polymer at temperatures between Tg and Tm of the polymer and it varies with temperature in this range. In some embodiments, the temperature can be in a range in which the crystal nucleation rate is larger than the crystal growth rate. In one embodiment, the temperature can be in a range in which the crystal nucleation rate is substantially larger than the crystal growth rate. For example, the temperature can be where the ratio of the crystal nucleation rate to crystal growth rate is 2, 5, 10, 50, 100, or greater than 100. In another embodiment, the temperature range may be in range between about Tg to about 0.2(Tm−Tg)+Tg.

Figure 2A:
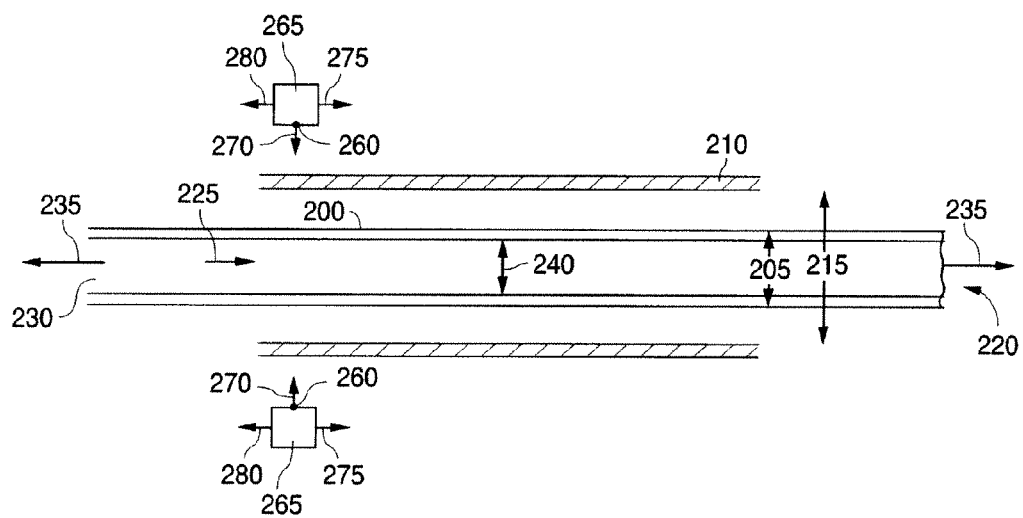
FIGS. 2A-C depict blow-molding of a polymeric tube.
Figure 2B:
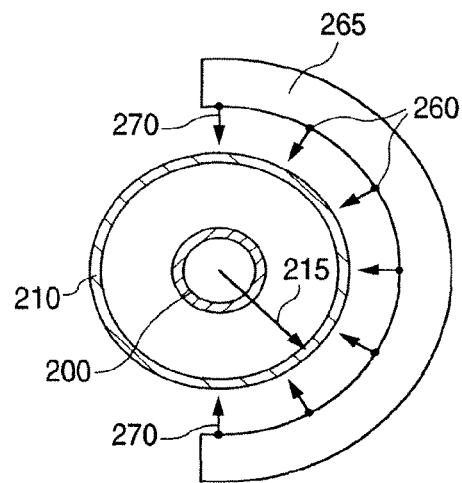
Figure 2C:
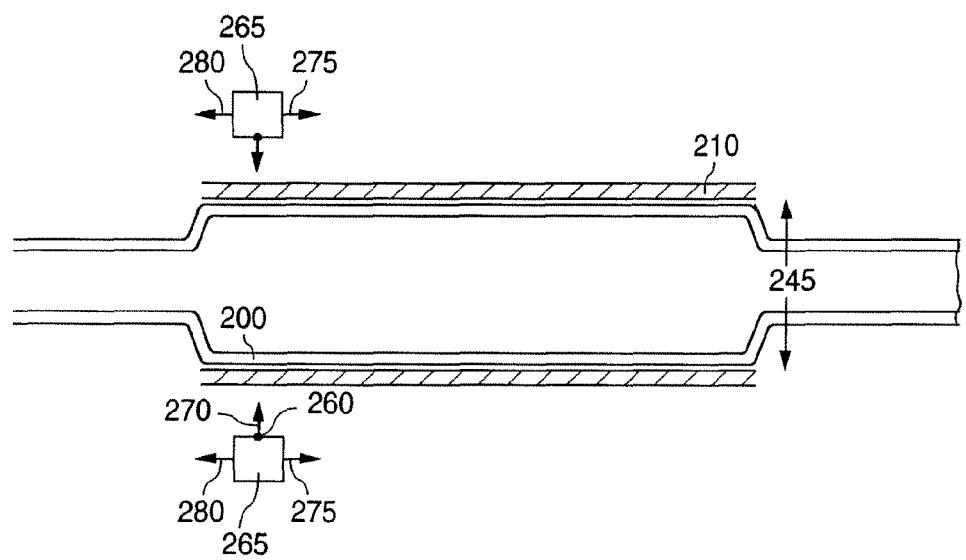

FIGS. 2A-C illustrate an embodiment of blow molding a polymer tube for use in manufacturing a stent. FIG. 2A depicts an axial cross-section of a polymer tube 200 with an outside diameter 205 positioned within a mold 210. FIG. 2B depicts a radial cross-section of polymer tube 200 and mold 210. Mold 210 may act to limit the radial deformation of polymer tube 200 to a diameter 215, the inside diameter of mold 205. Polymer tube 200 may be closed at a distal end 220. Distal end 220 may be open in subsequent manufacturing steps. A fluid may be conveyed, as indicated by an arrow 225, into an open proximal end 230 of polymer tube 200. A tensile force 235 is applied at proximal end 230 and a distal end 220.

Polymer tube 200 is heated by heating nozzles 260 on a support 265 that blow a heated gas as shown by arrows 270. Support 265 translates back and forth along the axis of the mold as shown by arrows 275 and 280. The increase in pressure inside of polymer tube 200, facilitated by an increase in temperature of the polymer tube, causes radial deformation of polymer tube 200, as indicated by an arrow 240. FIG. 2C depicts polymer tube 200 in a deformed state with an outside diameter 245 within mold 210.

Figure 3:
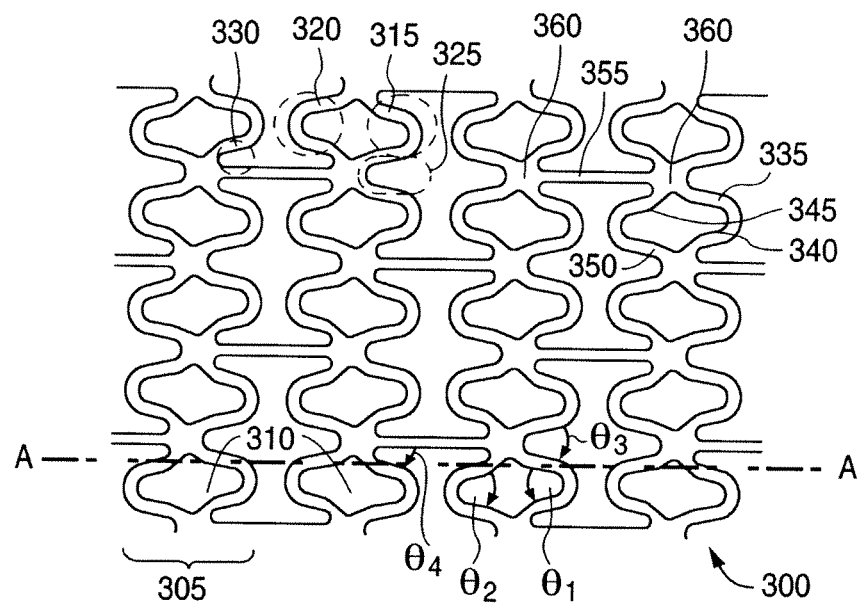
FIG. 3 depicts an exemplary stent pattern.

To illustrate the importance of orientation in a stent pattern, FIG. 3 depicts an exemplary stent pattern 300 for use with embodiments of a polymeric tube or a sheet. In an embodiment, stent pattern 300 can be cut from a polymeric tube using laser machining. Stent pattern 300 is shown in a flattened condition so that the pattern can be clearly viewed. When the flattened portion of stent pattern 300 is in a cylindrical form, it forms a radially expandable stent.

As depicted in FIG. 3, stent pattern 300 includes a plurality of cylindrical rings 305 with each ring including a plurality of diamond shaped cells 310. Embodiments of stent pattern 300 may have any number of rings 305 depending on a desired length of a stent. For reference, line A-A represents the longitudinal axis of a stent using the pattern depicted in FIG. 3. Diamond shaped cells 310 include bending elements 315 and 320. Stent pattern 300 can also includes bending elements 325 and 330. The angles of bending elements 315, 320, 325, and 330 correspond to angles $\theta_1$, $\theta_2$, $\theta_3$, and $\theta_4$. Angles $\theta_1$, $\theta_2$, $\theta_3$, and $\theta_4$ are 42, 42, 41, and 21 degrees, respectively. Diamond shaped cells 310 are made up of bar arms 335 and 340 that form bending element 315 and bar arms 345 and 350 that form bending element 320.

When stent 300 is crimped, bending elements 315, 320, 325, and 330 flex inward and angles $\theta_1$, $\theta_2$, $\theta_3$, and $\theta_4$ decrease, allowing the stent to be radially compressed. With respect to bending elements 315, 320, and 325, struts on either side of the bending elements bend toward each other. However, in bending element 330, the strut of the diamond-shaped element tends to bend toward the linking strut which tends to remain relatively parallel to the longitudinal axis during crimping.

Pattern 300 further includes linking arms 355 that connect adjacent cylindrical rings. Linking arms 355 are parallel to line A-A and connect adjacent rings between intersection 360 of cylindrically adjacent diamond-shaped elements 310 of one ring and intersection 360 of cylindrically adjacent diamond shaped elements 310 of an adjacent ring. As shown, linking elements connect every other intersection along the circumference.

Figure 4:
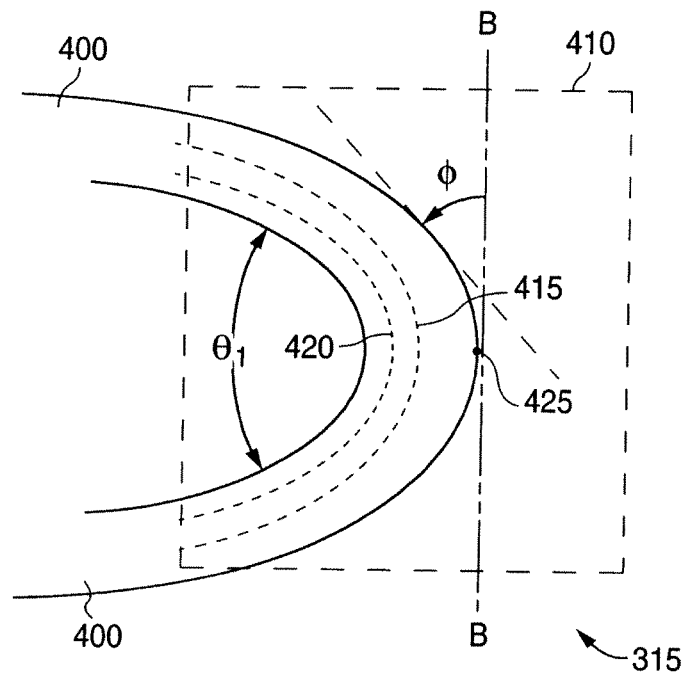
FIG. 4 depicts a bending element from the pattern in FIG. 3.

The curved portions of bending elements experience substantial stress and strain when a stent is crimped and deployed. Therefore high strength and toughness are very important in these regions. For example, a close-up view of bending element 315 is depicted in FIG. 4 to illustrate the direction of stress in a bending element. Compressive and outward radial stress on a stent cause substantially no strain in straight sections 400. However, such radial stresses result in relatively high stress and strain in curved portion 410 of bending element 315. For example, when a stent is expanded, angle $\theta_1$ of bending element 315 increases. The region above a neutral axis 415 experiences relatively high compressive stress and strain and the region below neutral axis 415 experiences relatively high tensile stress and strain. Alternatively, when a stent is crimped, angle $\theta_1$ of bending element 315 decreases and there is tensile stress and strain above neutral axis 415 and compressive stress and strain below neutral axis 415.

The tensile and compressive strain follow the axis or curvature of bending element 315, for example, line 420. Ideally, the most effective orientation to improve fracture toughness is along the length of the axis of the strut. However, radial expansion imparts orientation and fracture toughness along the circumferential direction, as shown by line B-B. An angle φ between a point on the axis of the stent and the circumferential direction B-B tends to decrease moving along bending element 315 from the straight sections 400 to an apex 425 of bending element 315.

An exemplary stent having the pattern of FIG. 3 can be cut from a poly(L-lactide) (PLLA) tube that is about 0.084 in inside diameter. A desired crimped diameter may be about 0.055 in and an expanded diameter about of 0.134 in. Such a stent can be fabricated from an extruded tube that is radially expanded between 200% and 400%. For a stent with the pattern shown in FIG. 3, and the dimensions provided above, cracks have been observed to form in the curved portion of bending elements upon expansion of the stent to the expanded diameter.

For a given radius of curvature, increasing angle $\theta_1$ of bending element 315 tends to decrease angle φ along the axis of bending element 315, making bending element 315 along curved portion 410 closer in orientation with the circumferential direction B-B. As a result, the strength and toughness of bending element 315 are increased when there is induced radial orientation in the stent. The relative orientation of points along the axis, angle φ, of a bending element also depends on the radius of curvature. Increasing the radius of curvature of bending element 315 also makes bending element 315 along curved portion 410 closer in orientation with the circumferential direction B-B.

Therefore, it is advantageous to decrease the relative orientation between the axis of bar arms or struts in curved portions and the circumferential direction in a fabricated stent. Certain embodiments of the invention include stents having bending elements with angles greater than about 80°, or more narrowly, greater than about 90°, or 110°. The stent may have an uncrimped or fabricated diameter that allows the stent to be crimped to a selected crimped diameter at which the bending elements have an angle between 0° to 50°, or more narrowly between 0° to 30°.

Figure 5:
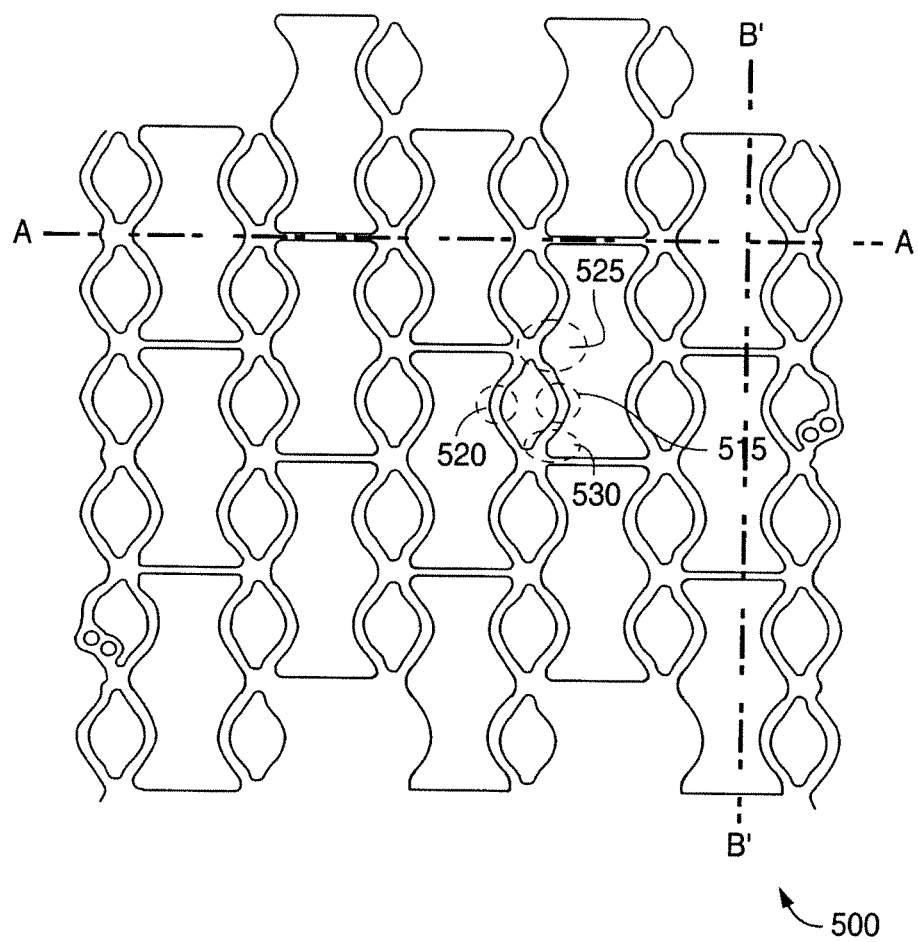
FIG. 5 depicts an alternative stent pattern.

FIG. 5 depicts a stent pattern 500 similar to pattern 300 in FIG. 3. The angles of bending elements 515, 520, 525, and 530 are about 113°, 113°, 116°, and 55°, respectively. Therefore, the orientation of points on the axis of the bending elements of pattern 500 are closer to the circumferential direction than that in stent pattern 300. The radii of curvature of bending element 515 and 520 can be between about 0.014 in and 0.02 in. The radii of curvature of bending element 525 can be between about 0.009 in and 0.013 in. The radii of curvature of bending element 525 can be between about 0.0026 in and 0.0035 in.

In an embodiment, the outside diameter (OD) of a fabricated stent can be between 0.07 in and 0.165 in. The crimped diameter of a stent having stent pattern 500 may be less than 0.06 in, 0.036 in, 0.032 in, or more narrowly less than 0.028 in.

In certain embodiments, it may be advantages to fabricate a stent from a tube that has been radial expanded to greater than 400%. As indicated above, cracks have been observed in high strain regions of stent fabricated from a tube expanded in the 200% to 400% range. In some embodiments, a stent may be fabricated from a tube that has been radial expanded to greater than 500%, 600%, 700%, or greater than 800%. The tube may be used to fabricate stents having a variety of patterns. In some embodiments, a stent with a stent pattern 500 can be fabricated from tube radially expanded to greater than 400%.

Such a stent may then show a greater increase in fracture toughness and stress over a stent fabricated from a tube radially expanded in a range between 200% and 400%. As a result, such a stent may have fewer or no cracks when expanded to an intended deployment diameter. Increasing the degree of expansion tends to impart greater strength and toughness. Thus, increasing the degree of expansion may extend the range of a diameter that a stent can be deployed.

Exemplary process conditions for expanding a PLLA tube between 400% and 700% include a temperature of heated air at the heat nozzle between 205° F. and 285° F. The heat nozzle air flow rate can be between about 60 and 65 SCFH (standard cubic feet per hour). The pressure of nitrogen conveyed into the tube can be between 177 psi and 250 psi. The tension applied axially to extend the tube can be between about 75 g and 105 g.

The advantages of expanding in a range greater than 400% is shown by the following example. A PLLA tube was extruded to an ID of 0.024 in and an OD of 0.074 in. The extruded tubing was radially expanded using blow molding 470% to an ID of 0.125 in and OD of 0.137 in. Five stents were prepared from the expanded tubing. The expanded tubing was laser cut to form a stents with a pattern similar to stent pattern 500 in FIG. 5. The stents were crimped, mounted on a catheter, and sterilized with E-beam radiation.

Figure 6:
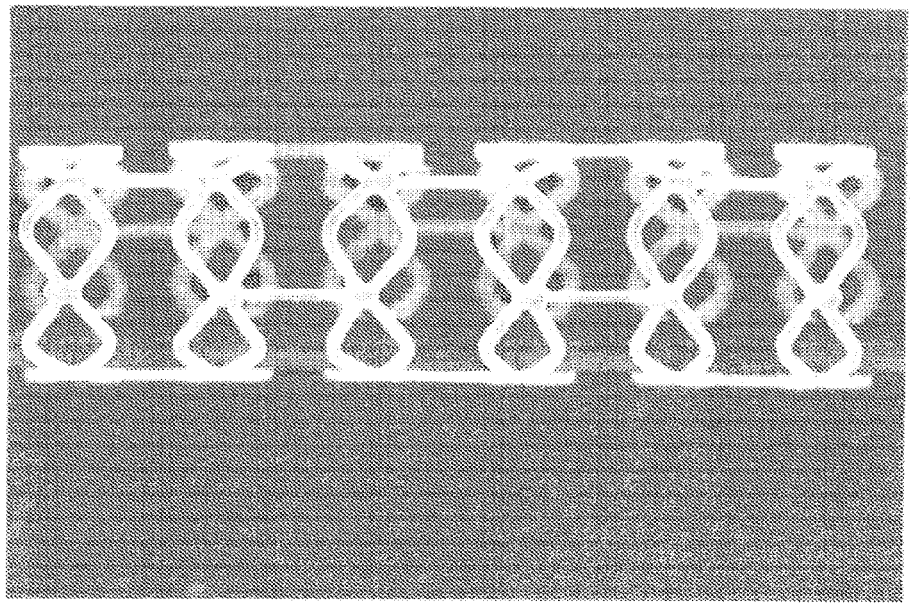
FIGS. 6-8 depict images of expanded stents.
Figure 7:
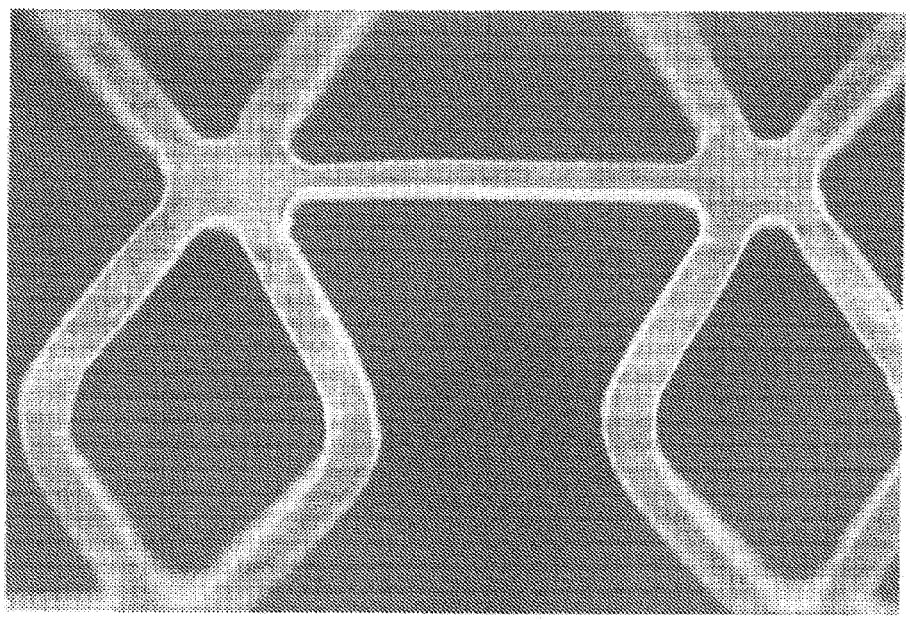

The stents were expanded by a balloon on the catheter in a 37° C. water bath to 0.138 in. The stents were removed and examined. FIGS. 6 and 7 show images of a stent expanded to 0.138 in. FIG. 6 depicts the entire stent and FIG. 7 depicts a close-up view. The stent appears to be substantially free of cracks.

Figure 8:
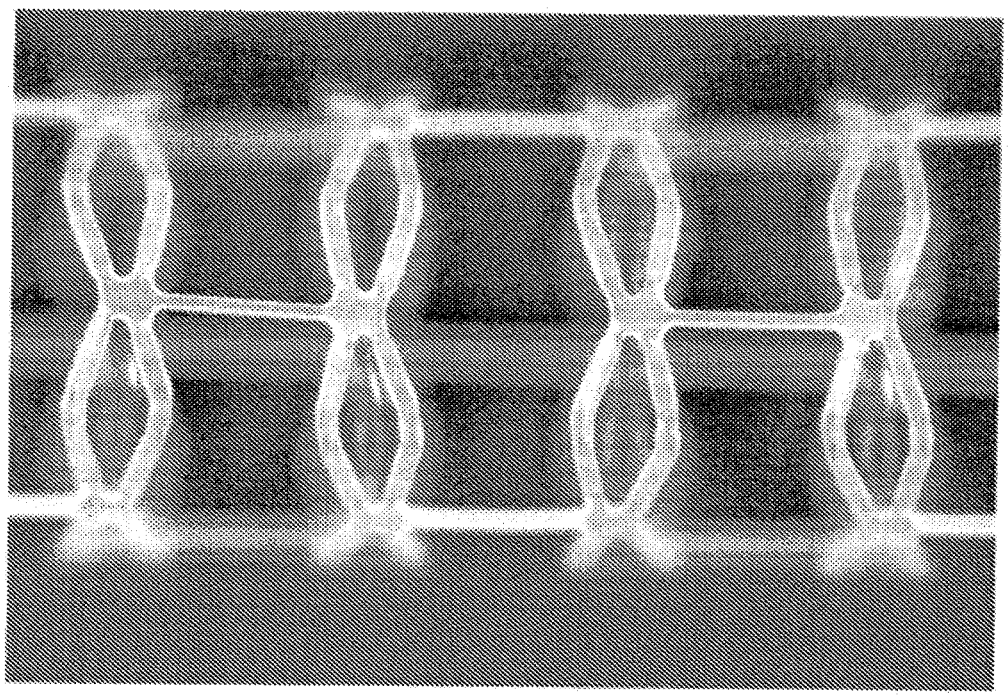

The stents were placed on another catheter and expanded further to 0.158 in. FIG. 8 depicts an image of this expanded stent which shows cracks forming in the high strain regions. The images demonstrate the effectiveness of increased biaxial orientation for the PLLA system.

As shown above, radial expansion above 400% can increases fracture toughness of an expanded stent. Radial expansion above 400% can also address other issues with polymeric stents, such as stent retention during crimping and physical aging during long term storage.

As discussed above, physical aging results in an increase in brittleness of a polymer which can result in cracking of struts upon crimping and deployment. Polymeric stents generally are stored below ambient temperatures to reduce or prevent physical aging the polymer that can cause cracking in stent struts during crimping and deployment. Stents can be stored in freezers at temperatures below 0° C. Storing the polymeric stents at low temperature reduces the segmental motions of polymer chains that result in densification.

In general, it would be desirable to store a polymeric stent close to ambient temperature. However, many polymers have Tg's low enough to allow significant long term aging or densification to occur during the time frame of long term storage, which can be a few days, a month, 3 months, 6 months, or more than 6 months. Although Tg is defined as the temperature at which the onset of segmental motion in the chains of the polymer occurs, the glass transition is not sharp or discontinuous for a polymer with amorphous regions. Rather, there is a gradual transition from the brittle to the ductile state corresponding to a gradual increase in segmental motion. Thus, even for polymers with Tg's above ambient temperatures, significant physical aging can occur during long term storage. Increasing the difference between the storage temperature and the Tg reduces the segmental motion of polymer chains which reduces or eliminate the effects of long term aging.

In addition, crimping of a polymeric stent at ambient temperatures can result in an outward recoil of the stent from the crimped radius, reducing stent retention on the catheter. Due to shape memory of the polymer, the stent recoils outward toward the fabricated diameter.

Such outward recoil can be reduced by heating the stent above ambient temperatures during crimping. However, it has been observed that elevated crimping temperatures can result in fracture of struts during crimping and upon deployment. Specifically, a PLLA stent fabricated from a polymeric tube expanded 300% from an extruded tube that is crimped at 50° C. results in fracture during deployment. This observed increase in mechanical damage to the stent is a result of stress relaxation of the polymer during the crimping process, due to the crimping being conducted close to the Tg of the polymer. This stress relaxation will result in greater experienced stress during the expansion of the stent during deployment. This will, in turn, result in a greater probability of cracking during the expansion of the stent.

Increasing the difference between the elevated crimping temperature and the Tg reduces the likelihood of cracking of struts.

In general, deforming a polymer form or construct can increase the Tg of the polymer. The increased order from orientation and induced crystallization caused by deformation tends to increase the temperature necessary for segmental motion of polymer chains, which corresponds to Tg.

For a given polymer system, the degree of deformation, or specifically, expansion of a polymeric tube, may be correlated with an increase in Tg. Thus, an increase in Tg can allow storage of the polymer form at a higher temperature with little or no negative effects of physical aging, or other visco-elastic phenomena. For example, the Tg can be increased to allow storage at ambient temperature. In addition, the Tg can be increased to allow crimping at a selected elevated temperature without cracking of stent struts.

In certain embodiments, a stent can be fabricated from a polymeric tube that allows crimping at a selected elevated temperature with no or substantially no cracking of struts. The polymeric tube can be radially expanded to a degree of expansion that allows crimping at the elevated temperature. The degree of expansion can be between 200% and 400%. In other embodiments, the degree of expansion can be between 400% and 800%. The selected elevated temperature can be at least 10° C., 20° C., 30° C., 40° C., or 50° C. below the Tg of the polymer.

In additional embodiments, a stent can be fabricated from a polymeric tube that allows long term storage at a selected temperature. For example, the temperature can be at or near an ambient temperature. The polymeric tube can be radially expanded to a degree of expansion that allows storage at the selected temperature with little or no negative effects of physical aging. As above, the degree of expansion can be between 200% and 400%. In other embodiments, the degree of expansion can be between 400% and 800%. The storage temperature can at least 30° C., 40° C., 50° C., 60° C., or 70° C. below the Tg of the polymer.

Differential scanning calorimetry (DSC) was used to study the increase in the Tg due the radial orientation induced by radial expansion. In general, DSC is a technique that may be used to identify thermal transitions in a polymer. Thermal transitions include, for example, crystallization and melting. A thermal transition in a polymer may be endothermic (sample absorbs heat) or exothermic (sample expels heat). Glass and melting transitions are exothermic and crystallization is endothermic.

In a typical DSC run, a polymer sample is heated at a constant rate. The heat inflow or outflow into the sample is controlled to keep the heating rate constant. When the sample undergoes a thermal transition, heat is either absorbed or expelled. At the glass transition and melting transition, heat flow into the sample decreases. When a polymer sample crystallizes, the heat flow into the sample increases.

The Tg of PLLA tubes was studied at 300% and 500% radial expansion. DSC runs were performed for two samples for each degree of expansion. For 500% radial expansion PLLA tubing was extruded to an ID of 0.021 in and an OD of 0.072 in. For 300% radial expansion, PLLA tubing was extruded to an ID of 0.018 in and an OD of 0.056 in. The extruded tubing was radially expanded using blow molding.

Figure 9:
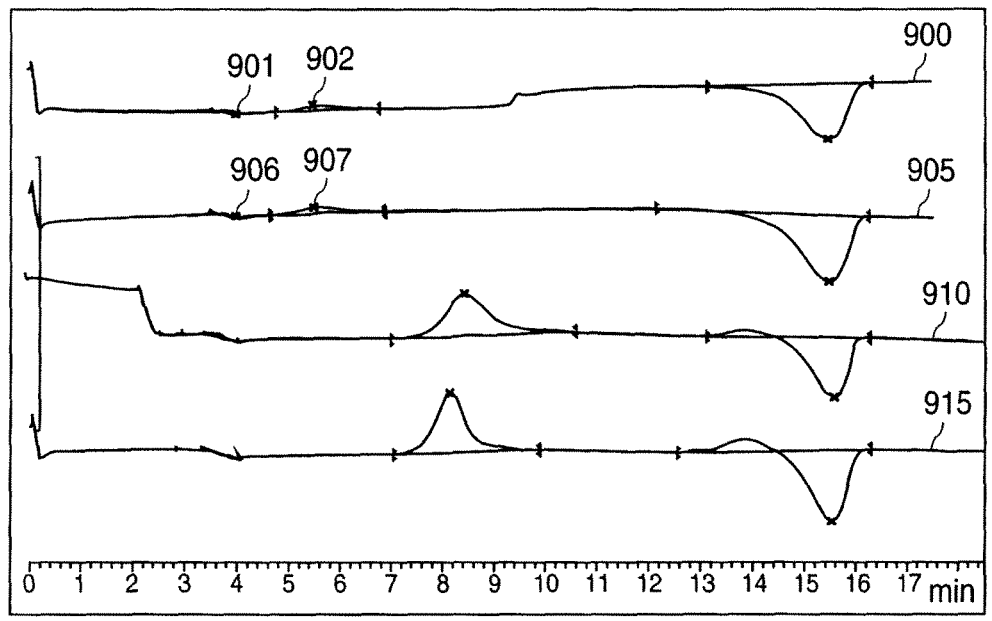
FIGS. 9-10 depict graphs of differential scanning calorimetry results.

FIG. 9 depicts the results of DSC runs for samples expanded to 300%. Curve 900 corresponds to the first sample and curve 905 corresponds to the second sample. Troughs 901 and 906 depict the glass transition, which is about 62° C. in each case. In addition, peaks 902 and 907 correspond to the crystallization transition of the polymer for the first and second samples, respectively.

The melted samples at the end of each run were quenched to a solid form. DSC runs were then performed on the quenched samples for comparison. These samples correspond to PLLA without induced orientation. Curve 910 corresponds to the first sample and curve 915 corresponds to the second sample.

Figure 10:
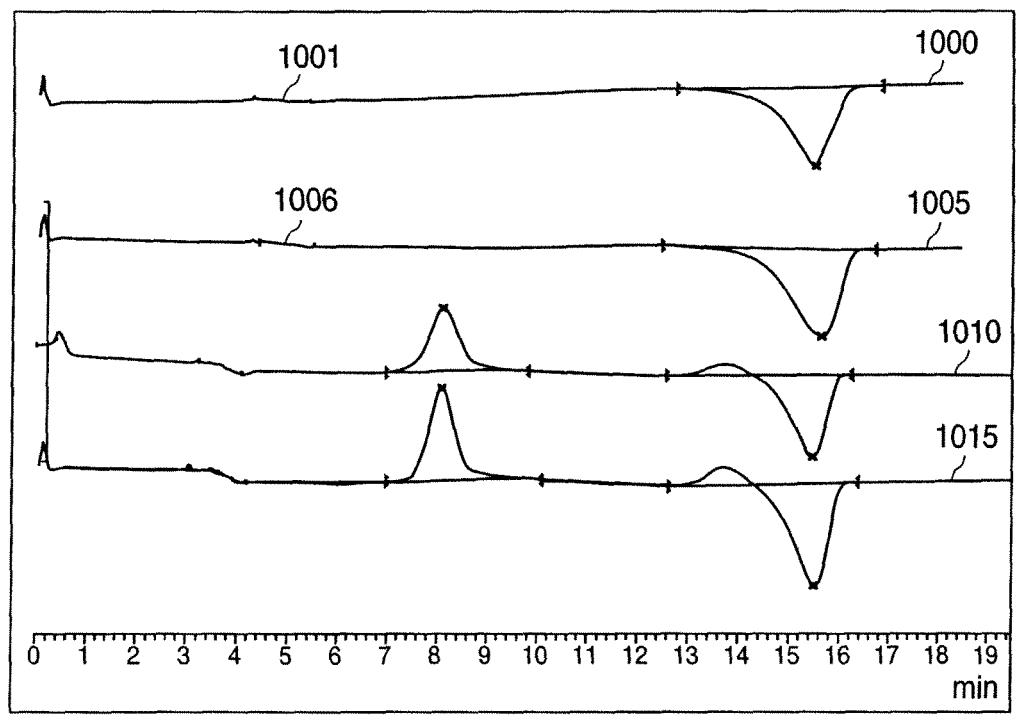

FIG. 10 depicts the results of DSC runs for samples expanded to 500%. Curve 1000 corresponds to the first sample and curve 1005 corresponds to the second sample. Troughs 1001 and 1006 depict the glass transition, which is about 71° C. in each case. Curves 1000 and 1005 do not have peaks analogous to peaks 902 and 907 in FIG. 9. This indicates that polymer of the samples expanded 500% was completely or almost completely crystallized due to stress induced crystallization. The high crystallinity reduces physical aging. The melted samples at the end of each run were quenched to a solid form. DSC runs were then performed on the quenched samples for comparison. These samples correspond to PLLA without induced orientation. Curve 1010 corresponds to the first sample and curve 1015 corresponds to the second sample.

Thus, the Tg increased from 62° C. to 71° C. from 300% to 500% radial expansion. A stent fabricated from a tube expanded 500% was crimped at 50° C. without strut fracture. Also, it is expected that the increase in Tg allows for an increase in storage temperature.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

The examples and experimental data set forth above are for illustrative purposes only and are in no way meant to limit the invention. The following examples are given to aid in understanding the invention, but it is to be understood that the invention is not limited to the particular materials or procedures of examples.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:
    radially expanding a polymer tube to about 400% to 800% of a starting diameter of the tube to increase the radial stiffness of the tube, wherein the fracture toughness of the radially expanded tube is enhanced by heating the tube to a temperature such that the crystal nucleation rate is at least twice the crystal growth rate while the tube is being radially expanded; and
    forming a plurality of rings from the radially expanded tube, wherein a ring forms a plurality of cells, each of the cells being defined by opposed ends separated by a circumferential distance and opposed bending elements extending between and connecting the opposed ends, and wherein an adjacent pair of rings are interconnected by a linking element.

2. The method of claim 1, the polymer having a glass transition temperature (Tg) and a melting temperature (Tm), wherein the tube has a temperature of about $Tg+0.2(Tm-Tg)$ when the tube is being radially expanded.

3. The method of claim 1, wherein the tube is a poly (L-lactide) tube.

4. The method of claim 1, wherein the tube is a poly (glycolic acid) tube.

5. The method of claim 1, wherein the cell is a diamond shaped cell.

6. The method of claim 1, wherein a first cell and a second, adjacent cell share an end.

7. The method of claim 1, wherein the linking element is a longitudinal linking element.

8. The method of claim 1, wherein the linking element is connected to one of the ends that form the cell.

9. A method of making a stent comprising:
    radially expanding a polymer tube at a temperature in which the crystal nucleation rate is at least twice the crystal growth rate to both increase radial stiffness and enhance fracture toughness in the polymer tube; and
    forming a plurality of rings from the radially expanded tube;
    wherein a ring includes a plurality of cells, each of which being defined by opposed ends separated by a circumferential distance and opposed bending elements extending between and connecting the opposed ends.

10. The method of claim 9, wherein the rings are interconnected by longitudinal linking elements.

11. The method of claim 10, wherein an end forms an end for each of two, adjacent cells of the ring.

12. The method of claim 11, wherein a longitudinal distance separating the opposed bending elements define a maximum width for the ring.

13. A method of making a stent comprising:
    radially expanding an extruded poly (L-lactide) tube to increase its radial stiffness, wherein a temperature of the tube during the radial expansion is within a range where a crystal nucleation rate is higher than a crystal growth rate so as to provide at least a desired fracture toughness for the radially stiffened tube; and
    forming the stent including forming a plurality of rings connected by linking elements from the radially stiffened tube;
    wherein the stent is configured for being crimped to a balloon and then radially expanded within a body lumen by the balloon such that the inflated balloon induces plastic deformation of the stent to maintain the stent in an expanded state within the body lumen.

14. The method of claim 13 wherein the temperature during radial expansion is about $Tg+0.2(Tm-Tg)$.

15. The method of claim 14 wherein the stent is laser cut from the expanded poly (L-lactide) tube.

* * * * *